United States Patent [19]

Hamazaki et al.

[11] 4,318,923
[45] Mar. 9, 1982

[54] BENZAMINOETHYLPHENOXYCY-CLOHEXYLACETIC ACID DERIVATIVES

[75] Inventors: Yasuhiko Hamazaki; Nobuo Ishiyama; Toshiyuki Yamamoto; Kenji Seri; Reiko Sato, all of Tokyo, Japan

[73] Assignee: Kaken Chemical Co., Ltd., Tokyo, Japan

[21] Appl. No.: 243,447

[22] Filed: Mar. 13, 1981

[30] Foreign Application Priority Data

Apr. 10, 1980 [JP] Japan .................. 55-46243

[51] Int. Cl.³ .................. A61K 31/24; C07C 101/30
[52] U.S. Cl. .................. 424/309; 424/246;
424/248.54; 424/263; 424/275; 424/282;
424/285; 424/316; 424/319; 260/340.5 R;
260/347.3; 260/347.4; 544/169; 546/335;
549/77; 548/180; 560/42; 562/451
[58] Field of Search .................. 560/42; 562/451;
424/309, 316, 319, 246, 248.54, 282, 285, 263,
275; 260/340.5 R, 347.3, 347.4; 544/169;
546/335; 549/77; 548/180

[56] References Cited

U.S. PATENT DOCUMENTS

| | | | |
|---|---|---|---|
| 3,781,328 | 12/1973 | Witte et al. | 560/42 |
| 4,151,303 | 4/1979 | Witte et al. | 560/42 |
| 4,153,728 | 5/1979 | Wolff et al. | 562/451 |
| 4,207,341 | 6/1980 | Hubner et al. | 560/42 |
| 4,214,094 | 7/1980 | Kamiya et al. | 562/451 |

OTHER PUBLICATIONS

Witte et al., Chem. Absts., 79, 18434(k), 1973.

Primary Examiner—G. T. Breitenstein
Attorney, Agent, or Firm—Oblon, Fisher, Spivak, McClelland & Maier

[57] ABSTRACT

Benzaminoethylphenoxycyclohexylacetic acid derivatives having the formula

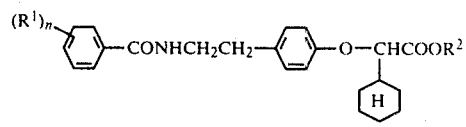

wherein $R^1$ represents hydrogen atom, a halogen atom, hydroxyl group, a lower alkyl group or a lower alkoxy group; n is 1 or 2; and $R^2$ represents hydrogen atom, a lower alkyl group which can have a substituent of phenyl group, a lower alkoxycarbonyl group, 3,3,5-trimethylcyclohexyloxycarbonyl group or a heterocyclic group; hexadecyl group; phenyl group which can have a substituent of a lower alkyl group, a lower alkoxy group, a lower alkoxycarbonyl group or a halogen atom; a cyclohexyl group or α-[4-(4-chlorobenzaminoethyl) phenoxy]-α-cyclohexylacetoxycyclohexyl group a antihyperlipidemic compositions thereof.

6 Claims, No Drawings

BENZAMINOETHYLPHENOXYCYCLOHEXYLACETIC ACID DERIVATIVES

BACKGROUND OF THE INVENTION

1. Field of the Invention

The present invention relates to novel benzaminoethylphenoxycyclohexylacetic acid derivatives, to preparations of such compounds and to antihyperlipidemic agents comprising such compounds as the active ingredients.

2. Description of the Prior Arts

It has been known to clinically use Bezafibrate, Clofibrate and analogous compounds; nicotinic acid derivatives; hormones such as protein assimilation steroids; unsaturated aliphatic acid such as linoleic acid; cholestyramine and β-sitosterols as antihyperlipidemic agents.

The inventors have studied and proposed various oxyacetic acid derivatives and their effects to humanbodies and have found that certain oxyacetic acid derivatives have desired antihyperlipidemic properties.

SUMMARY OF THE INVENTION

It is an object of the present invention to provide novel benzaminoethylphenoxycyclohexylacetic acid derivatives which are effective for remedy of hyperlipidemia.

It is the other object of the present invention to provide a process for producing novel benzaminoethylphenoxycyclohexylacetic acid derivatives.

The foregoing and other objects of the present invention have been attained by providing benzaminoethylphenoxycyclohexylacetic acid derivatives having the formula

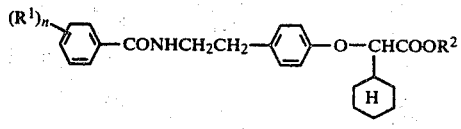

wherein $R^1$ represents hydrogen atom, a halogen atom, hydroxyl group, a lower alkyl group or a lower alkoxy group; n is 1 or 2; and $R^2$ represents hydrogen atom, a lower alkyl group which can have a substituent of phenyl group, a lower alkoxycarbonyl group, 3,3,5-trimethylcyclohexyloxycarbonyl group or a heterocyclic group; hexadecyl group; phenyl group which can have a substituent of a lower alkyl group, a lower alkoxy group, a lower alkoxycarbonyl group or a halogen atom; a cyclohexyl group or α-[4-(4-chlorobenzaminoethyl)phenoxy]-α-cyclohexylacetoxycyclohexyl group which have excellent antihyperlipidemic activity.

DETAILED DESCRIPTION OF THE PREFERRED EMBODIMENTS

The inventors have studied preparations of various cyclohexylacetic acid derivatives and pharmacological characteristics of the cyclohexyl acetic acid derivatives.

As a result, it has been found that the novel benzaminoethylphenoxycyclohexylacetic acid derivatives having (I) have excellent antihyperlipidemic activity.

In the formula (I) as $R^1$ and $R^2$, a halogen atom can be fluorine, chlorine, bromine or iodine atom; a lower alkyl group and a lower alkoxy group can have straight or branched alkyl group, and a lower alkyl group can be methyl, ethyl, propyl or butyl group; a lower alkoxy group can be methoxy, ethoxy, propoxy or butoxy group; a lower alkoxycarbonyl group can be methoxycarbonyl, ethoxycarbonyl, propoxycarbonyl or butoxycarbonyl group; a heterocyclic group can be furyl, thienyl, morphorino, benzothiazole, pyridyl or 3,4-methylenedioxyphenyl group.

The benzaminoethylphenoxycyclohexylacetic acid derivatives having the formula (I)

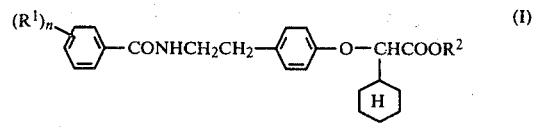

wherein $R^1$, $R^2$ and n are defined above can be produced by reacting a benzaminoethylphenol compound having the formula (II)

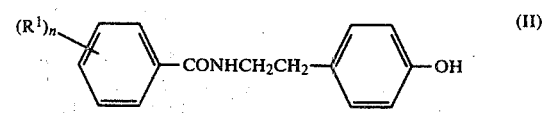

wherein $R^1$ and n are defined above with α-halogenocyclohexyacetic acid compound having the formula (III)

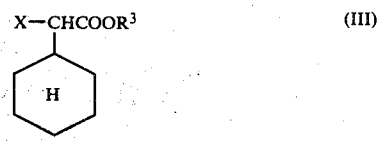

wherein X represents a halogen atom and $R^3$ represents the groups of $R^2$ defined above; if necessary, followed by hydrolyzing the product or interesterifying the product.

The compounds having the formula (III) wherein X is —I, —Br, or —Cl are preferably used. In the reaction, an equimolar amount of α-halogeno-cyclohexylacetate (III) is usually reacted with the compound (II). However, it is possible to use an excess of either the compound (II) or the compound (III).

The solvents are organic solvents inert under the reaction conditions such as dimethyl formamide and acetone. A mixed solvent can be used for the reaction.

For example, the reaction can be accelerated by adding a base such as potassium carbonate, sodium carbonate, sodium methylate or sodium ethylate.

It is possible to separate the reaction product obtained by reacting the base with the compound (II) from the reaction system and then, to react the compound (III) with the separated reaction product.

The reaction conditions such as temperature, time and pressure can be decided depending upon the starting materials, the solvent and the base.

The reaction is usually completed, at room temperature, in 1 to 2 days or at 100° to 180° C. for 5 to 20 hours.

The corresponding carboxylic acids can be obtained by hydrolyzing the benzaminoethylphenoxycyclohexylacetic acid ester (I). The hydrolysis can be carried out by the conventional processes. It is preferable to carry out the hydrolysis in an alkaline condition with an aqueous solution of sodium hydroxide or potassium hydroxide with an alcohol.

The resulting benzaminoethylphenoxycyclohexylacetic acid or ester thereof can be converted into the corresponding ester by reacting it with a chlorinating agent such as thionyl chloride and phosphorus trichloride to form the corresponding carboxylic acid chloride and further reacting the product with a compound having the formula

R²—OH wherein R² is defined above, in the presence of a base such as pyridine or triethylamine; or by reacting it with a compound having the formula

R²—X wherein R² and X are defined above; or by reacting it with a compound having the formula

R²—OH in the presence of a esterificating agent such as tosyl acid and tosyl chloride.

The reaction products (I) can be separated and purified by conventional separating methods such as concentration, particularly concentration under reduced pressure; distillation; particularly distillation under a reduced pressure; fractional distillation; the adjustment of alkalinity or acidity; solvent extraction; crystallization; recrystallization; inversion and chromatography.

The novel benzaminoethylphenoxycyclohexylacetic acid derivatives (I) have excellent antihyperlipidemic activity and are effective in practice as an antihyperlipidemic agent for hyperlipidemia remedy.

The benzaminoethylphenoxycyclohexylacetic acid derivatives (I) have low toxicity and they do not cause hepatic disease (hepatitis) which is found by the administration of ethyl-α-(p-chlorophenoxy)isobutyrate (Clofibrate) or [2-{4-[2-(4-chlorobenzamide)-ethyl]-phenoxy}-2-methylpropionic acid](Bezafibrate).

The antihyperlipidemic agents of the present invention comprising the benzaminoethylphenoxycyclohexylacetic acid derivatives (I) can be orally administered in the form of tablets, capsules, powder or granules; and they can also be parenterally administered in the form of injectable solutions, suppositories or pellets.

The benzaminoethylphenoxycyclohexylacetic acid derivative (I) can be combined with other antihyperlipidemic agents, a hypotensive agent or an anticoagulant agent.

The dose of the benzaminoethylphenoxycyclohexylacetic acid derivative (I) is usually in a range of 25 to 2500 mg., preferably 100 to 1000 mg. per day per adult in oral dose.

The invention will be further illustrated by the following examples.

EXAMPLE 1

Ethyl α-[4-(4-chlorobenzaminoethyl)phenoxy]-α-cyclohexyacetate: (Compound No. 1)

Into 50 ml. of dimethylformamide containing 3.2 g. (0.0479 mol) of sodium ethylate, 11 g. (0.04 mol) of N-(4-chlorobenzoyl)-tyramine was added and further 39.8 g. (0.16 mol) of ethyl α-bromocyclohexylacetate was added and the mixture was stirred at 170° C. for 10 hours. After the reaction, dimethylformamide was distilled off under a reduced pressure and ice water was added and the reaction product was extracted with benzene. The extracted benzene layer was washed with 2% NaOH aq.sol. and then with water and was dehydrated over sodium sulfate and then, benzene was distilled off under a reduced pressure. The residue was recrystallized from a mixed solvent of ethanol and n-hexane to obtain 5.7 g. of ethyl α-[4-(4-chlorobenzaminoethyl)phenoxy]-α-cyclohexylacetate (yield: 32.5%).

Melting point: 103°–104° C.

IR Spectrum (KBr): $\gamma$(cm$^{-1}$): 3325 (NH), 1740 (C=O), 1640 (C—NH)
         ‖
         O In accordance with the same process, the products shown in Table 1 were produced by using the corresponding starting materials. The physical properties of the products are also shown in Table 1.

TABLE 1

(R¹)ₙ—⟨benzene⟩—CONHCH₂CH₂—⟨benzene⟩—O—CHCOOR²
                                              |
                                              cyclohexyl (H)

| Comp. No. | (R¹)ₙ | R² | Melting point (°C.) | IR $\gamma_{C=0}^{KBr}$ (cm$^{-1}$) |
|---|---|---|---|---|
| 2 | 2-Cl | C₂H₅ | 89–90 | 1760, 1655 |
| 3 | 3-Cl | C₂H₅ | 106–107 | 1755, 1630 |
| 4 | 2-F | C₂H₅ | 85–86 | 1745, 1650 |
| 5 | 3-F | " | 104–105 | 1750, 1640 |
| 6 | 4-F | " | 111–112 | 1755, 1640 |
| 7 | 2-CH₃ | " | 86–87 | 1755, 1630 |
| 8 | 3-CH₃ | " | 80–81 | 1740, 1630 |
| 9 | 4-CH₃ | " | 88–89 | 1755, 1645 |
| 10 | 2-OCH₃ | " | Oil | $\gamma_{C=0}^{Oil}$ 1740, 1645 |
| 11 | 3-OCH₃ | " | 78–79 | 1740, 1640 |
| 12 | 4-OCH₃ | " | 120–121 | 1755, 1640 |
| 13 | H | " | 95.5–97 | 1755, 1640, 1740 |
| 14 | 4-i-C₃H₇ | " | 87–88 | 1755, 1640, 1745 |
| 15 | 4-n-C₄H₉ | " | 61–62 | 1760, 1645, 1745 |
| 16 | 4-t-C₄H₉ | " | 125–126 | 1760, 1640, 1750 |
| 17 | 4-Cl | n-C₄H₉ | 92–93 | 1750, 1645 |
| 18 | 4-Cl | n-C₁₆H₃₃ | 109–110 | 1740, 1645 |

EXAMPLE 2

α-[4-(4-chlorobenzaminoethyl)phenoxy]-α-cyclohexylacetatic acid: (Compound No. 19)

Into 70 ml. of 70% ethanol containing 2 g. of sodium hydroxide, 5.7 g. (0.0128 mol) of the ester obtained in Example 1 was dissolved and the mixture was refluxed for 30 minutes and then, the solvent was distilled off under a reduced pressure and then water was added and the mixture was acidified with 5% HCl and the reaction product was extracted with benzene. The extracted benzene layer was washed with water and dehydrated over sodium sulfate and benzene was distilled off and the residue was recrystallized from ethanol to obtain 3.8 g. of α-[4-(4-chlorobenzaminoethyl)phenoxy]-α-cyclohexylacetic acid (yield: 71.7%).

Melting point: 187°–188° C.

IR Spectrum (KBr): γ(cm$^{-1}$): 3320 (NH); 1735 (C=O); 1640 (CONH).

In accordance with the same process, the products shown in Table 2 were produced by using the corresponding starting materials. The physical properties of the products are also shown in Table 2.

TABLE 2

$(R^1)_n$—⟨phenyl⟩—CONHCH$_2$CH$_2$—⟨phenyl⟩—O—CHCOOR$^2$
                                                           |
                                                    (cyclohexyl)
                                                           H

| Comp. No. | $(R^1)^n$ | $R^2$ | Melting point (°C.) | IR $\gamma_{C=O}^{KBr}$ (cm$^{-1}$) |
|---|---|---|---|---|
| 20 | 2-Cl | H | 126–127 | 1740, 1650 |
| 21 | 3-Cl | " | 165–166 | 1730, 1640 |
| 22 | 2-F | " | 153–154 | 1740, 1650 |
| 23 | 3-F | " | 175–176 | 1740, 1620 |
| 24 | 4-F | " | 186–187 | 1740, 1620 |
| 25 | 2-CH$_3$ | " | 138–139 | 1740, 1620 |
| 26 | 3-CH$_3$ | " | 181–182 | 1730, 1620 |
| 27 | 4-CH$_3$ | " | 195–196 | 1740, 1620 |
| 28 | 2-OCH$_3$ | " | | 1750, 1630 |
| 29 | 3-OCH$_3$ | " | 205–206 | 1730, 1720 |
| 30 | 4-OCH$_3$ | " | 213–214 | 1730 |
| 31 | H | " | 189.5–190.5 | 1740, 1720, 1645 |
| 32 | 4-i-C$_3$H$_7$ | " | 155–156 | 1740, 1640 |
| 33 | 4-n-C$_4$H$_9$ | " | 154–155 | 1740, 1650 |
| 34 | 4-t-C$_4$H$_9$ | " | 165–166 | 1740, 1640 |

EXAMPLE 3

Cyclohexyl α-[4-(4-chlorobenzaminoethyl)phenoxy]-α-cyclohexylacetate: (Compound No. 35)

Into 6 ml. of pyridine, 1.65 g. (0.004 mol) of α-[4-(4-chlorobenzaminoethyl)phenoxy]-α-cyclohexylacetic acid was dissolved, and then, 0.40 g. (0.004 mol) of cyclohexanol was added and then, 0.95 g. (0.005 mol) of tosyl chloride was added and the mixture was heated at 80°–90° C. for 2 hours to react them. The reaction mixture was poured into ice water and the precipitate was separated by a filtration and washed with water and the reaction product was recrystallized from a mixed solvent of ethanol and water to obtain 1.7 g. of the object compound (yield: 86.1%).

Melting point: 104°–105° C.

IR Spectrum: $\gamma_{C=O}^{KBr}$: 1760, 1750, 1650 cm$^{-1}$

EXAMPLE 4

2-Ethoxycarbonylphenyl α-[4-(4-chlorobenzaminoethyl)phenoxy]-α-cyclohexylacetate: (Compound No. 36)

In 15 ml. of dichloroethane, 1.65 g. (0.004 mol) of α-[4-(4-chlorobenzaminoethyl)phenoxy]-α-cyclohexylacetic acid obtained in Example 2 was suspended and then, 2 ml. of thionyl chloride was added. The mixture was refluxed for 1 hour to react them. The solvent was distilled off under a reduced pressure and 10 ml. of dichloroethane was added to the residue and the solvent was distilled off under a reduced pressure. The residue was admixed with 1 ml. of pyridine and 0.73 g. (0.0044 mol) of ethyl salicylate dissolved in 0.5 ml. of pyridine was added to react them for 30 minutes. The reaction mixture was cooled and added into 5% HCl aqueous solution. The reaction product was extracted with benzene and the benzene layer was washed with water, with 5% NaOH aq. sol. and then with water and the benzene layer was dehydrated over sodium sulfate. Benzene was distilled off and the residue was recrystallized from ethanol to obtain 1.6 g. of the object compound (yield: 71.5%).

Melting point: 125°–126° C.

IR Spectrum: $\gamma_{C=O}^{KBr}$: 1770, 1740, 1640 cm$^{-1}$

In accordance with the process of Example 3 or 4, the products shown in Table 3 were produced by using the corresponding starting materials. The physical properties of the products are also shown in Table 3.

TABLE 3

$(R^1)_n$—⟨phenyl⟩—CONHCH$_2$CH$_2$—⟨phenyl⟩—O—CHCOOR$^2$
                                                           |
                                                    (cyclohexyl)
                                                           H

| Comp. No. | $(R^1)^n$ | $R^2$ | Melting point (°C.) | IR $\gamma_{C=O}^{KBr}$ (cm$^{-1}$) |
|---|---|---|---|---|
| 37 | 4-Cl | —⟨phenyl⟩ | 148–149 | 1775, 1650 |
| 38 | " | —CH(COOEt)—⟨phenyl⟩— | Oil | Oil $\nu_{C=O}$ 1755, 1650 |
| 39 | " | —⟨cyclohexyl-H⟩—O$_2$C—CH(cyclohexyl-H)—O—⟨phenyl⟩—CH$_2$—CH$_2$NHCO—⟨phenyl⟩—Cl | 82–83 | 1755, 1740, 1650 |
| 40 | " | —CH$_2$—⟨furan⟩ | 88–89 | 1765, 1650 |

TABLE 3-continued $$(R^1)_n\text{-Ar-CONHCH}_2\text{CH}_2\text{-Ar-O-CHCOOR}^2$$
(with cyclohexyl on CH)

| Comp. No. | $(R^1)_n$ | $R^2$ | Melting point (°C.) | IR $\gamma_{C=O}^{KBr}$ (cm$^{-1}$) |
|---|---|---|---|---|
| 41 | " | –C$_6$H$_4$–Cl | 152–153 | 1775, 1650 |
| 42 | " | –C$_6$H$_4$–CH$_3$ | 131–132 | 1775, 1650 |
| 43 | " | –CH$_2$–(pyridyl) | 122–123 | 1750, 1660 |
| 44 | " | –CH$_2$–(benzodioxole) | 133–134 | 1745, 1650 |
| 45 | " | –CH(Et)–C$_6$H$_5$ | 124–125 | 1750, 1660, 1650 |
| 46 | " | –CH$_2$CH$_2$–N(morpholino) | Oil | $\nu_{C=O}^{Oil}$ 1750, 1650 |
| 47 | " | –CH(CH$_3$)–(benzothiazolyl) | 152–153 | 1760, 1645 |
| 48 | 3-Cl | –C$_6$H$_{11}$ | Oil | $\gamma_{C=O}^{Oil}$ 1750, 1650 |
| 49 | 3-Cl | –C$_6$H$_4$–COOEt | Oil | $\gamma_{C=O}^{Oil}$ 1780, 1740, 1660 |
| 50 | 4-Cl | –CH(C$_6$H$_5$)CO$_2$–(2,2,6,6-tetramethylcyclohexyl) | 59–60 | 1760, 1655 |

Preparation 1

A 400 g. of ethyl α-[4-(4-chlorobenzaminoethyl)-phenoxy]-α-cyclohexylacetate, 400 g. of fine powdery silicondioxide and 185 g. of corn starch were uniformly mixed and charged in a kneader and 1000 ml. of 3% aqueous solution of hydroxypropyl cellulose was added and the mixture was kneaded. The mixture was granulated by passing it through the 16 mesh screen to form uniform granules which comprises an antihyperlipidemic agent.

Preparation 2

A 400 g. of α-[4-(4-chlorobenzaminoethyl)phenoxy]-α-cyclohexylacetic acid, 400 g. of lactose and 175 g. of potato starch were uniformly mixed and charged in a kneader and 3% aqueous solution of hydroxypropyl cellulose was added and the mixture was kneaded and granulated by passing through a 16 mesh screen and 0.3% of magnesium stearate was added and the mixture was compressed to form tablets which comprise an antihyperlipidemic agent.

Test 1

The antihyperlipidemic activity in rats with dietary hyperlipidemia.

In the tests, Wister type male rats (weight: 140 g.) were used in groups of 6 each.

A feed containing 2% of cholesterol, 1% of sodium cholate and 5% of coconut oil was given for 4 days to cause hyperlipidemia.

Each active ingredient was suspended in a 1% aqueous solution of Tween 80 (® polyoxyethylene sorbitane monoalkylate) and the suspension was orally administered in a dose of 100 mg./kg. once daily for 4 days starting with the supply of the cholesterol supplemented diet.

After 24 hours from the administration, blood was sampled and the concentration of total cholesterols in blood-plasma was measured by the method described in Clinical chemistry Vol. 22 page 393 (1968) and the concentration of triglyceride (neutral fat) was measured by Fletcher method (Clinica Chimica Acta)Vol. 10 page 451 (1964).

Percent liver weight was given by extracting liver and measuring each weight of liver and calculating a ratio of the liver weight to a total weight.

As the active ingredients, the compounds of the invention shown in Table and ethyl-α-(p-chlorophenoxy)-isobutylate having the formula

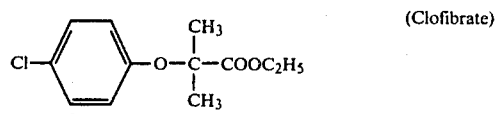
(Clofibrate)

and 2-{4-[2-(4-chlorobenzamide)ethyl]phenoxy}2-methylpropionic acid

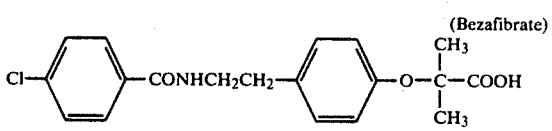
(Bezafibrate)

The test results are shown in Table 4.

TABLE 4

| Compound No. | Antihyperlipidemic activity (%) (p.o. 100 mg/kg) | | Percent weight increase of liver (%) |
|---|---|---|---|
| | Cholesterol | Triglyceride | |
| 1 | 44 | 62 | 8.8 |
| 2 | 77 | 66 | 0 |
| 3 | 33 | 21 | 0.9 |
| 4 | 45 | 45 | 0 |
| 5 | 53 | 69 | 0 |
| 6 | 54 | 45 | 0 |
| 7 | 42 | 63 | 2.1 |
| 8 | 23 | 42 | 0 |
| 9 | 14 | 0 | 0.5 |
| 10 | 30 | 40 | 0 |
| 11 | 31 | 56 | 0 |
| 12 | 28 | 0 | 0 |
| 13 | 14 | 72 | 4.5 |
| 14 | 18 | 23 | 0 |
| 15 | 16 | 20 | 0 |
| 16 | 11 | 18 | 0 |
| 17 | 53 | 48 | 12.8 |
| 18 | 47 | 42 | 10.3 |
| 19 | 46 | 68 | 4.5 |
| 20 | 65 | 89 | 1.6 |
| 21 | 57 | 99 | 6.2 |
| 22 | 41 | 35 | 0.9 |
| 23 | 51 | 0 | 9.7 |
| 24 | 65 | 25 | 9.6 |
| 25 | 62 | 89 | 10.2 |
| 26 | 25 | 64 | 7.3 |
| 27 | 4.2 | 41.1 | 6.4 |
| 28 | 32 | 43 | 0 |
| 29 | 61 | 53 | 0 |
| 30 | 40 | 54 | 10.7 |
| 31 | 49 | 90 | 9.7 |
| 32 | 21 | 27 | 0 |
| 33 | 19 | 25 | 0 |
| 34 | 16 | 23 | 0 |
| 35 | 37 | 42 | 2.8 |
| 36 | 42 | 47 | 3.0 |
| 37 | 39 | 42 | 3.9 |
| 38 | 46 | 50 | 4.2 |
| 39 | 43 | 48 | 3.8 |
| 40 | 48 | 49 | 4.0 |
| 41 | 47 | 51 | 5.2 |
| 42 | 40 | 36 | 3.8 |
| 43 | 33 | 37 | 2.6 |
| 44 | 47 | 52 | 4.2 |
| 45 | 38 | 41 | 3.9 |
| 46 | 41 | 42 | 4.3 |
| 47 | 32 | 39 | 2.9 |
| 48 | 45 | 50 | 4.2 |
| 49 | 42 | 48 | 3.9 |
| 50 | 40 | 51 | 0.9 |
| Clofibrate | 38 | 39 | 24.2 |
| Bezafibrate | 0 | 36 | 32.8 |

Test 2

In the acute toxicity tests, male mice (weight: 22 to 25 g.) were used in groups of 10 each.

Each active ingredient was dissolved in olive oil and the solution was orally administrated in a volume corresponding to the body weight.

$LD_{50}$ was calculated by the area method from the mortal percent after 72 hours from the administration.

The $LD_{50}$ of the Compound No. 1, 2, 5, 6 and 19 were respectively greater than 4,000 mg./kg.

We claim:

1. A benzaminoethylphenoxycyclohexylacetic acid derivative having the formula

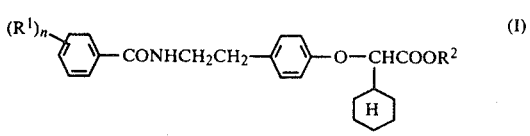

wherein $R^1$ represents hydrogen atom, a halogen atom, hydroxyl group, a lower alkyl group or a lower alkoxy group; n is 1 or 2; and $R^2$ represents hydrogen atom, a lower alkyl group which can have a substituent of phenyl group, a lower alkoxycarbonyl group, 3,3,5-trimethylcyclohexyloxycarbonyl group or a heterocyclic group selected from the group consisting of furyl, thienyl, morphorino, benzothiozole, pyridyl or 3,4 methylenedioxyphenyl; hexadecyl group; phenyl group which can have a substituent of a lower alkyl group, a lower alkoxy group, a lower alkoxycarbonyl group or a halogen atom; a cyclohexyl group or α-[4-(4-chlorobenzaminoethyl)phenoxy]-α-cyclohexylacetoxycyclohexyl group.

2. A benzaminoethylphenoxycyclohexylacetic acid derivative according to claim 1 which has the formula (I) wherein $R^1$ represents hydrogen atom, a halogen atom, hydroxyl group, a lower alkyl group or a lower alkoxy group; n is 1 or 2; $R^2$ represents a lower alkyl group.

3. A benzaminoethylphenoxycyclohexylacetic acid derivative according to claim 1 which has the formula (I) wherein $R^1$ represents hydrogen atom, a halogen atom, hydroxyl group, a lower alkyl group or a lower alkoxy group; n is 1 or 2; $R^2$ represents hexadecyl group or a lower alkyl group having a substituent of phenyl group, a lower alkoxycarbonyl group, 3,3,5-trimethylcyclohexyloxy carbonyl group or a heterocyclic group selected from the group consisting of furyl, thienyl, morphorino, benzothiozole, pyridyl or 3,4 methylenedioxyphenyl.

4. A benzaminoethylphenoxycyclohexylacetic acid derivative according to claim 1 which has the formula (I) wherein $R^1$ represents hydrogen atom, a halogen atom, hydroxyl group, a lower alkyl group or a lower alkoxy group; n is 1 or 2; $R^2$ represents hydrogen atom.

5. A benzaminoethylphenoxycyclohexylacetic acid derivative according to claim 1 which has the formula (I) wherein $R^1$ represents hydrogen atom, a halogen atom, hydroxyl group, a lower alkyl group, a lower alkoxy group; n is 1 or 2; $R^2$ represents phenyl group which can have a substituent of a lower alkyl group, a lower alkoxy group, a lower alkoxycarbonyl group or a halogen atom.

6. An antihyperlipidemic composition which comprises an effective amount of a benzaminoethylphenoxycyclohexylacetic acid derivative according to claim 1 which has the formula (I) as an active ingredient and an inert pharmaceutical carrier.

* * * * *